United States Patent [19]

Becker

[11] Patent Number: 4,643,733
[45] Date of Patent: Feb. 17, 1987

[54] PERMANENT RECONSTRUCTION IMPLANT AND METHOD OF PERFORMING HUMAN TISSUE EXPANSION

[76] Inventor: Hilton Becker, 818 Lakeside Dr., North Palm Beach, Fla. 33408

[21] Appl. No.: 481,912

[22] Filed: Apr. 4, 1983

[51] Int. Cl.$^4$ .................. A61F 2/12; A61F 2/02; A61B 19/00
[52] U.S. Cl. .................. 623/8; 128/1 R; 623/11
[58] Field of Search .............. 3/1, 1.2, 36; 128/1 R, 128/DIG. 25; 623/7, 8, 11

[56] References Cited

U.S. PATENT DOCUMENTS

| | | | |
|---|---|---|---|
| 3,600,718 | 8/1971 | Boone | 3/36 |
| 3,831,583 | 8/1974 | Edmunds et al. | 128/1 R |
| 3,852,833 | 12/1974 | Koneke et al. | 3/36 |
| 3,863,622 | 2/1975 | Buuck | 128/1 R |
| 3,883,902 | 5/1975 | Lynch | 3/36 |
| 4,095,295 | 6/1978 | Lake | 3/36 |
| 4,157,085 | 6/1979 | Austad | 128/1 R |
| 4,217,889 | 8/1980 | Radovan et al. | 128/1 R |

OTHER PUBLICATIONS

"Silastic Varifil Mammary Implant (Inflatable Design)" Dow Corning Brochure—Bulletin: 51-358, Dow Corning Australia Pty Ltd, 21 Tattersall Rd., Blacktown, N.S.W. 2148 (4 pages) Oct. 1977.
Heyer Schulte Inflatable Mammary Prostheses (Brochure) (102031-002-02-280), Hyer-Schulte Corp., Subsidiary of American Hospital Supply Corp., 600 Pine Ave., Goleta, CA 93017 (9 pages).

Primary Examiner—Ronald L. Frinks

[57] ABSTRACT

A delayed filling permanent reconstruction implant comprising a inflatable flexible prosthesis having an inlet opening, a normally closed valve in the inlet opening, a filling tube having one end detachably connected to the prosthesis at the inlet opening and operable when in the inlet opening to open the valve, and a reservoir connected to the other end of the filling tube. In addition, a method of performing human tissue expansion and providing a permanent reconstruction implant comprising the steps of providing a permanent prosthesis having an inlet opening, a normally closed valve in the opening, providing a filling tube having one end adapted for insertion into the inlet opening to open the valve and having a self-sealing reservoir at its other end, surgically placing the prosthesis in the area to be expanded and reconstructed and placing the filling tube and reservoir beneath the skin adjacent the prosthesis with the tube one end in the inlet opening, gradually expanding the prosthesis by percutaneous fluid injections into the reservoir, and detaching the reservoir and filling tube from the prosthesis and allowing the prosthesis to remain permanently in position.

8 Claims, 13 Drawing Figures

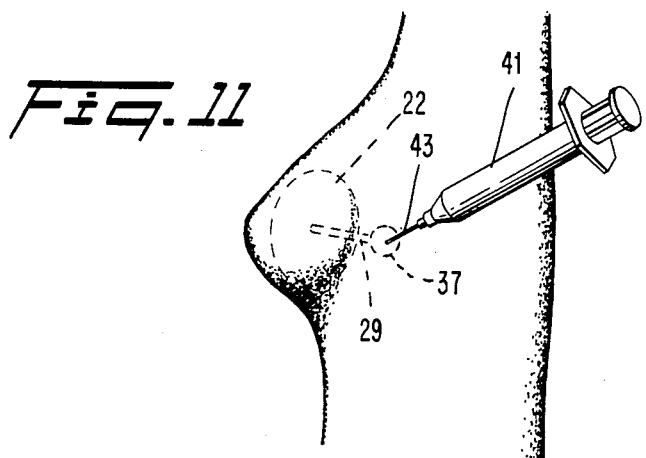
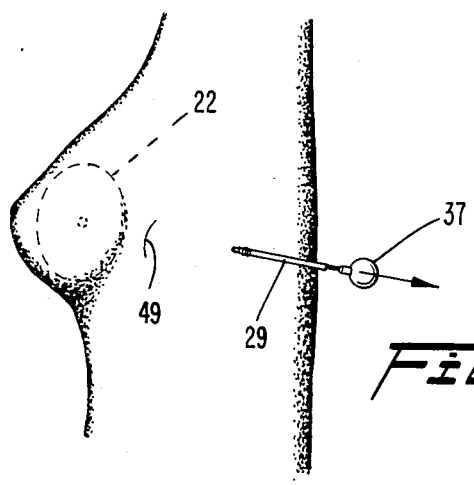
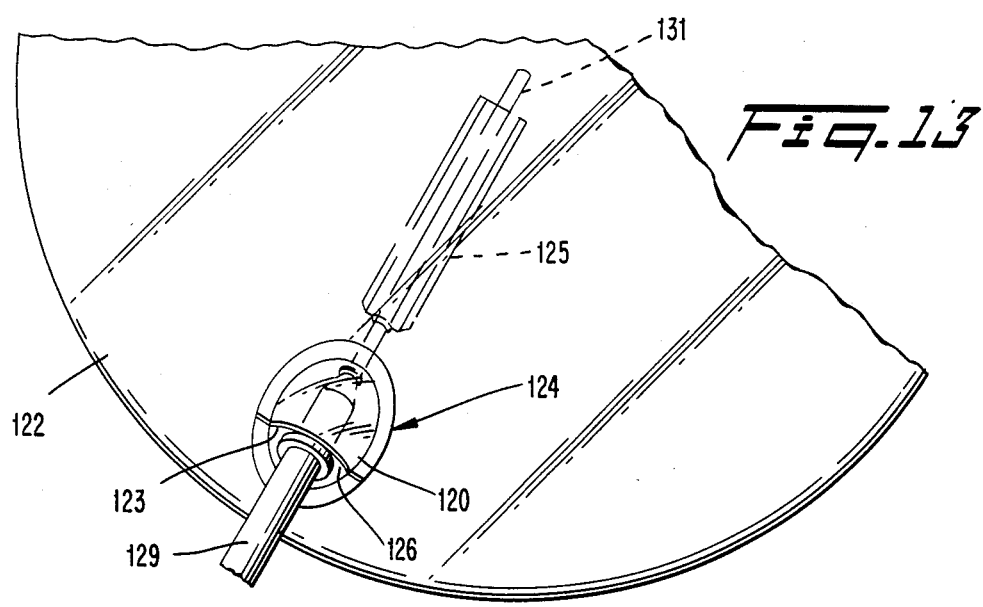

PERMANENT RECONSTRUCTION IMPLANT AND METHOD OF PERFORMING HUMAN TISSUE EXPANSION

BACKGROUND OF THE INVENTION

The present invention relates to reconstruction implants, and more particularly to an implant which is adapted both to perform skin and tissue expansion and to serve as a permanent reconstruction implant. The invention also relates to a method of performing delayed filling of an implant once placed beneath the tissues for reconstruction. The present invention will be described specifically with reference to breast reconstruction implants where it finds particular use. However, it will be understood that this invention applies to other reconstruction where expansion and a permanent implant are required. Also, the device of this invention is particularly useful in situations where it is desirable to carry out delayed tissue expansion, i.e., days, weeks, or even months after implantation.

Temporary expansion devices for expanding or stretching skin and tissue at the breast area following mastectomy have been developed. These devices and the techniques for using them are described in Radovan, *Breast Reconstruction After Mastectomy Using The Temporary Expander,* Plastic and Reconstruction Surgery, 195 (1982). See also, Radovan, et al., U.S. Pat. No. 4,217,889.

Skin and tissue expansion after removal of breast tissue often is required for successful breast reconstruction and to obtain proper symmetry of the reconstructed breast. Expansion must be carried out slowly over a long period of time in order to save the skin because circulation to this area is greatly reduced after tissue removal. Preferably, the skin is overexpanded and then allowed to contract over the permanent implant.

Current temporary tissue expanders employ an expandable envelope having an unflexible or stiffly flexible base. A reservoir is fixed to the envelope by a flexible tubing. The envelope is surgically implanted and the reservoir is surgically placed beneath the skin near the breast. The envelope is expanded gradually, over a period of time, by percutaneous injections of fluid, e.g., saline, into the reservoir.

When the desired skin expansion is achieved, usually about 10% greater than the final breast size, the expander, reservoir and tubing are surgically removed and a permanent implant inserted.

Several successful versions of permanent breast implants are marketed by American Heyer-Schulte corporation and include an inflatable prosthesis having an inlet opening provided with a valve. A filling tube is detachably connected to the prosthesis at the inlet opening and when in position, holds the valve open. The prosthesis is surgically implanted, often after an expansion device has been employed as described above, and the implant is filled with fluid, e.g., saline, which is injected through the filling tube. When the implant is filled, the filling tube is detached, allowing the valve to close, and the implant remains in position permanently.

It will be appreciated that use of the prior art temporary expanders and permanent implants requires two major surgical procedures, the first to insert the temporary expander, and the second to remove the expander and insert the permanent implant. This results in a great deal of discomfort and anxiety to the patient and exposes the patient to two chances of infection, and additional risk of a second operative procedure, and additional expense.

In addition, it is often desirable that expansion of an implant not be performed immediately following surgery but that the wound be allowed to heal first. Here, again, currently available implants require a second major surgical procedure for implant placement which is undesirable for the same reasons advanced above.

SUMMARY OF THE INVENTION

The present invention overcomes the problems and disadvantages of the prior art by providing a singular device which functions both as an expander and as a permanent implant. The device of this invention requires only a single major surgical procedure. A reservoir is detachably connected by a filling tube to the implant and the reservoir and tube can be placed beneath the skin nearby. The implant is gradually expanded by percutaneous injections into the reservoir. Upon completion of the expansion procedure, the reservoir and filling tube can be easily detached from the implant and removed through a single small incision over the reservoir, or through the origional incision.

A valve is provided at an inlet opening in the implant. The valve is held open by the filling tube and automatically closes upon detachment of the filling tube. The implant then remains in place permanently. The device of this invention is ready made for delayed expansion, i.e., where a healing period is desired before expansion begins. The prosthesis can be implanted at the time of original surgery, for example, mastectomy, and can remain fully or partially collapsed until the wound has healed. The complication of wound breakdown caused by excessive pressure from a large implant is avoided. Expansion can then be performed as desired and the need for a second major surgical procedure is obviated.

Additional objects and advantages of the invention will be set forth in part in the description which follows, and in part will be obvious from the description, or may be learned by practice of the invention. The objects and advantages may be realized and attained by means of the instrumentalities and combinations particularly pointed out in the appended claims.

To achieve the objects and in accordance with the purpose of the invention, as embodied and broadly described herein, the subcutaneous expander and permanent reconstruction implant of this invention comprises an inflatable, flexible plastic prosthesis adapted to be implanted beneath human tissue, the prosthesis having an inlet opening, a normally closed valve in the inlet opening, a filling tube having one end detachably connected to the prosthesis at the inlet opening and operable when in the opening to open the valve, and a reservoir connected to the other end of the filling tube, whereby the prosthesis can be controllably expanded after implantation by percutaneous injection of fluid into the reservoir which fluid passes through the filling tube into the prosthesis, the filling tube and the reservoir being readily detachable from the prosthesis upon achieving the desired expansion thereof, whereupon the valve closes and the prosthesis remains permanently implanted.

Broadly, the prosthesis is expanded by percutaneous injection of fluid into the reservoir which is adapted to be placed beneath the skin adjacent the implant. The reservoir and filling tube are detachable from the prosthesis and removable through a small single incision.

Desirably, the reservoir and the prosthesis are constructed substantially entirely of a relatively soft and flexible material and the inlet opening and valve are located at a lateral position of the prosthesis.

In another aspect, the present invention relates to a method of performing human tissue expansion and providing a permanent reconstruction implant comprising the steps of providing a permanent prosthesis having an inlet opening, a normally closed valve in the opening, providing a filling tube having one end adapted for insertion into the inlet opening to open the valve and having a self-sealing reservoir at its other end, surgically placing the prosthesis in the area to be expanded and reconstructed and placing the filling tube and reservoir beneath the skin adjacent the prosthesis with the tube one end in the inlet opening, gradually expanding the prosthesis by percutaneous fluid injections into the reservoir, and detaching the reservoir and filling tube from the prosthesis and allowing the prosthesis to remain permanently in position.

The accompanying drawings which are incorporated in and constitute a part of this specification, illustrate embodiments of the invention and, together with the description, serve to explain the principles of the invention.

BRIEF DESCRIPTION OF THE DRAWINGS

FIG. 11 is a view similar to FIG. 10 and showing a percutaneous injection of fluid being made to the reservoir and the implant expanded;

FIG. 12 is a view similar to FIG. 11 and showing the reservoir and filling tube detached from the implant and removed from beneath the skin; and FIG. 13 is a view showing a modified form of valve and filling tube.

DESCRIPTION OF THE PREFERRED EMBODIMENTS

Reference will now be made in detail to the present preferred embodiments of the invention, examples of which are illustrated in the accompanying drawings.

Figure 1:
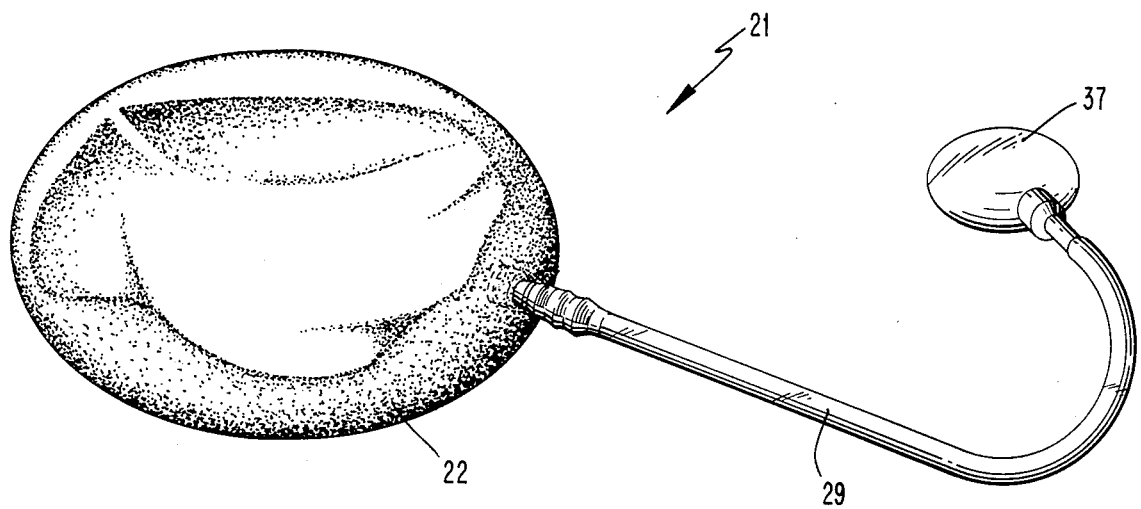
FIG. 1 is a perspective view showing a prosthesis or implant, filling tube, and reservoir constructed according to the invention, the prosthesis shown being in the collapsed condition.
Figure 2:
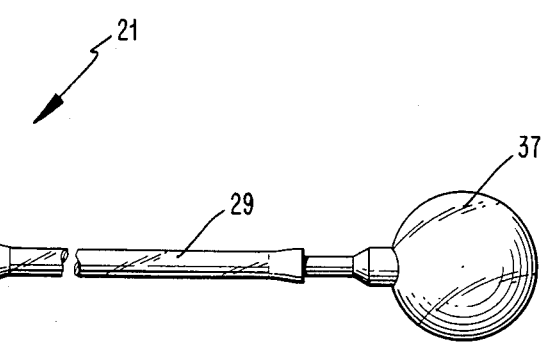
FIG. 2 is a plan view of the structure of FIG. 1, the prosthesis being shown expanded.
Figure 3:
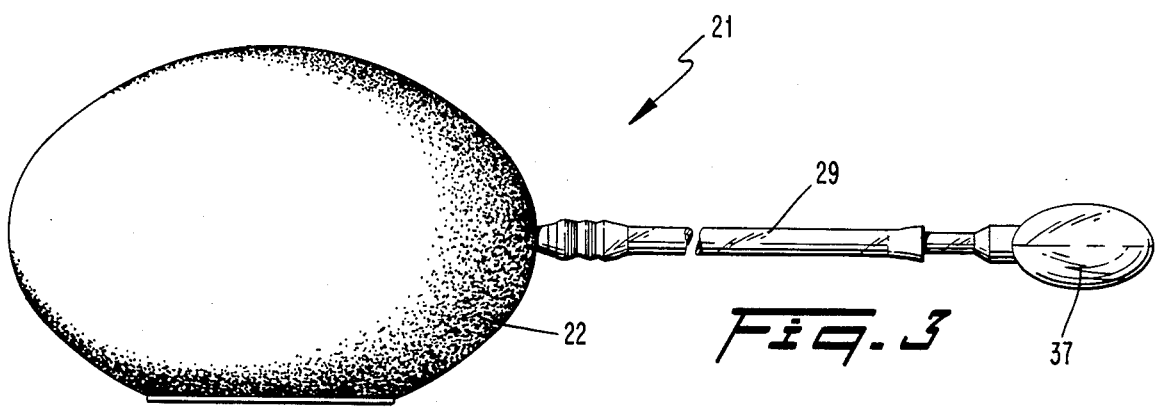
FIG. 3 is a side view of the structure of FIG. 2.
Figure 4:
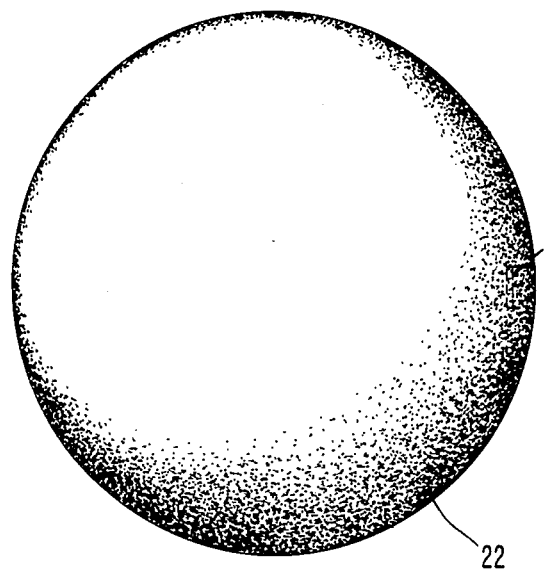
FIG. 4 is a view similar to FIG. 2 with the parts detached.
Figure 4:
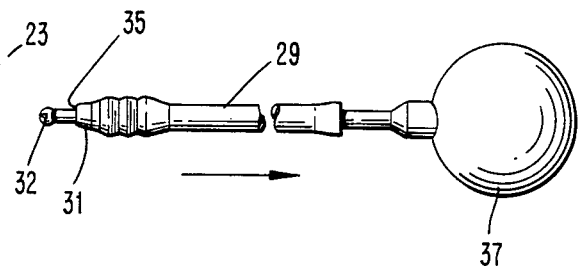
Figure 5:
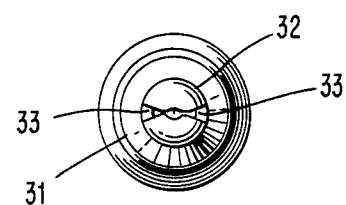
FIG. 5 is an enlarged end view of the filling tube of FIG. 4.

A preferred embodiment of expander and reconstruction implant is shown in FIGS. 1-3 and is represented by the numeral 21. The expander and implant comprises an inflatable, flexible plastic prosthesis adapted to be implanted beneath human tissue, the prosthesis having an inlet opening, and a normally closed valve in the inlet opening. As embodied herein, the expander and implant 21 comprises an inflatable, flexible plastic bag 22 which is provided with an inlet opening 23 having a valve 24 disposed therein. (See also FIGS. 6 and 7). Desirably, the inlet opening 23 and valve 24 are disposed at a lateral side of the bag 22 for a purpose to be described.

Figure 6:
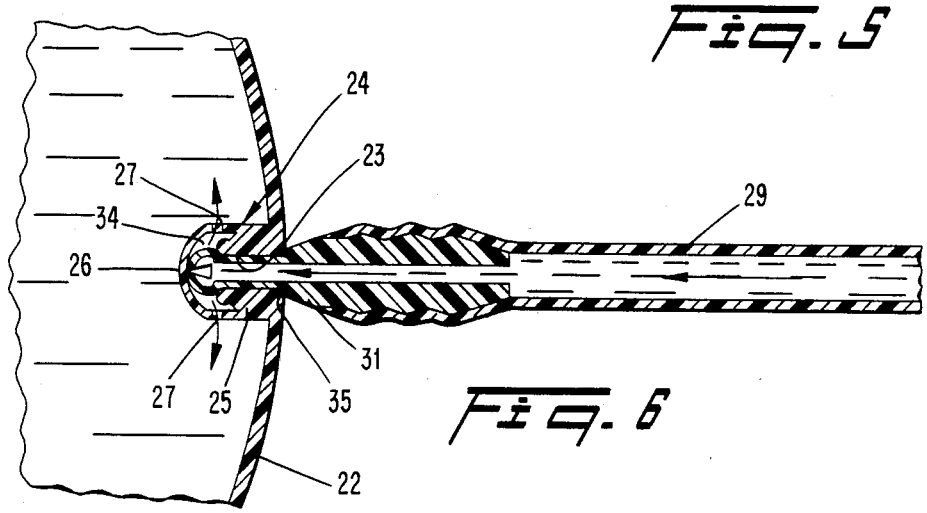
FIG. 6 is an enlarged sectional view showing the filling tube and prosthesis valve attached.
Figure 7:
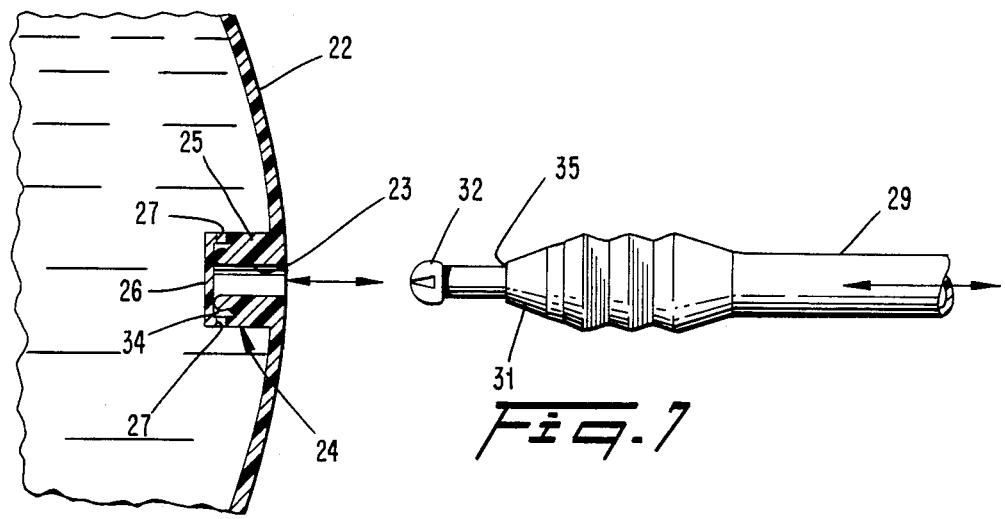
FIG. 7 is a view similar to FIG. 6 with the parts detached.

In the embodiment shown in FIGS. 1-7, the valve 24 is a diaphragm valve which includes a tube 25 which may be formed integrally with and extend inwardly of the bag 22. A diaphragm 26 is connected to and extends across the inner end of the tube 25 and is provided with a plurality of lateral openings 27. As shown in FIG. 7, the diaphragm 26 normally engages and covers the inner end of the tube 25 so that the valve 24 is normally closed.

As further embodied herein, the inflatable bag 22 is adapted to be implanted beneath a human breast. Desirably, the illustrated implant is surgically placed in a submuscular pocket beneath the pectoralis major muscle after a mastectomy has been performed. The bag implant 22 can be constructed of any known nontoxic, flexible plastic material which is substantially impermeable to liquid. Suitable materials include silicone elastomers having successive cross-linked layers of silicone elastomer, each cross-linked layer being joined to the adjacent layer. The expanded volume of the bag 22 will vary in size according to the desired breast size from approximately 150 cc to approximately 700 cc.

In accordance with the invention, a filling tube has one end detachably connected to the implant 22 at the inlet opening 23 and is operable when in the inlet opening, to open the valve 24. A reservoir is connected to the other end of the filling tube, whereby the implant can be controllably expanded after implantation by percutaneous injections of fluid into the reservoir, which fluid passes through the filling tube into the implant.

As embodied herein, a filling tube 29 has one end 31 adapted to be inserted into the inlet opening 23 and to extend into the valve tube 25. The tube end 31 fits snugly into the valve tube 19 and is frictionally retained therein. If desired, the tube end 31 can be bulb-shaped as at 32, as shown, so that when fully inserted in the opening 15, the bulb end 32 projects into a recess 34 in the valve tube 19 as shown in FIG. 6. The tube end 31 is removable from the valve tube 19 by applying a suitable pulling force on the tube 20.

When fully inserted, the tube end 31 engages the diaphragm 26 and unseats it from the end of the valve tube 25 as shown in FIG. 6. Slots 33 are formed in the tube end 31 so that in this position, fluid delivered through the tube 29 passes through the slots 33 and enters the implant 13 through the valve openings 27. A shoulder 35 limits the distance the tube end 31 can be inserted into the opening 23 and prevents rupture of the diaphragm 26.

As further embodied herein, a reservoir 37 is connected to the opposite end of the filling tube. Preferably, the reservoir 37 is substantially entirely constructed of a relatively soft and flexible material which facilitates easy removal from beneath the skin as described below, although it can be substantially hemispherical in configuration and joined to a substantially rigid base. The reservoir 37 is constructed of a suitable nontoxic material so that it can be implanted together with the filling tube 29 beneath the skin.

Also, the reservoir 37 is constructed of a self-sealing material so that fluid can be injected into the reservoir using a needle and the reservoir will seal upon removal of the needle. Desirably, the injections of fluid into the reservoir can be made percutaneously after implantation of the bag 22, filling tube 29 and reservoir 37 so that the prosthesis can be controllably expanded by injecting fluid into the reservoir 37. Such fluid passes through the filling tube 29 and then into the implant 22. Fluid can also be removed percutaneously from the implant 22 using a syringe with a needle penetrating the reservoir 37.

In accordance with the invention, the filling tube 29 and the reservoir 37 are readily detachable from the prosthesis 13 upon achieving the desired expansion thereof whereupon the valve 24 closes and the prosthesis 13 remains permanently implanted. As embodied herein, the filling tube 29 and the reservoir 37 can be permanently attached to one another. As described above, the filling tube end 31 is detachably connected to the implant 22 at the inlet opening 15 so that upon application of a suitable pulling force, the tube end 31 pulls out of the valve tube 25. Since the implant 22 will have been in place for an extended time period, some four to eight weeks, some encapsulation will have occurred making it easy to detach the tube 29 by pulling on it.

The filling tube 29 and reservoir 37 are implanted beneath the skin of the patient and can be removed by making a simple incision above the reservoir only large enough to withdraw the reservoir. With the device of this invention, the original incision used to implant the prosthesis can be used to withdraw the reservoir and filling tube thereby avoiding a second incision and a second scar. The lateral position of the inlet opening on the prosthesis 13 makes detachment of the filling tube 29 and reservoir 37 relatively easy and minimizes the required length of filling tube 29. As shown in figure 7, the inlet opening 23 forms a relatively smooth exterior surface upon detachment of the filling tube 29 from the opening 23.

Expansion of the skin flaps and the pectoralis major muscle after mastectomy normally must be carried out gradually over a period of four to eight weeks. This is to prevent damage to the skin flaps since blood circulation to this area is greatly reduced when breast tissue is removed in mastectomy. Desirably, the skin flaps are overexpanded beyond the desired size and shape. After overexpansion, fluid is removed percutaneously from the implant 22 through the reservoir 37 until the desired size is achieved. This results in a smoother, more natural contour in the reconstructed breast and prevents damage to the skin flaps. Expansion and later contraction of the implant is carried out easily with the present invention since fluid can be injected and withdrawn percutaneously through the implanted reservoir 37.

An important feature of the present invention is that only one major surgical procedure is required, i.e., for implantation of the prosthesis 22. The attached filling tube 29 and reservoir 37 are placed beneath the skin near the implant and remain in place only so long as is required for expansion of the prosthesis 22, as described above, normally four to eight weeks. When the desired size has been achieved, usually after overexpansion and then removal of some of the fluid from the prosthesis, it is then only necessary to make a small incision over the reservoir 37 such as is shown at 49 in FIG. 12 which is large enough to remove it from beneath the skin. Often, the original incision can be used here resulting in only one scar. A simple pulling force on the reservoir 37 causes the filling tube 29 to pull out of the valve tube 25. The reservoir 37 and filling tube 29 are then easily removed from beneath the skin through the small incision 49. The valve 24 automatically closes upon detachment of the tube 29 and the prosthesis remains permanently in position and a second major surgical procedure is avoided.

In addition, the device of this invention is useful in other implants where delayed expansion is desirable. As in many breast implants, it may be that the implant should not be expanded until the wound has had a chance to heal. The implant and the detachable filling tube and reservoir of this invention readily accomodate this.

Figure 8:
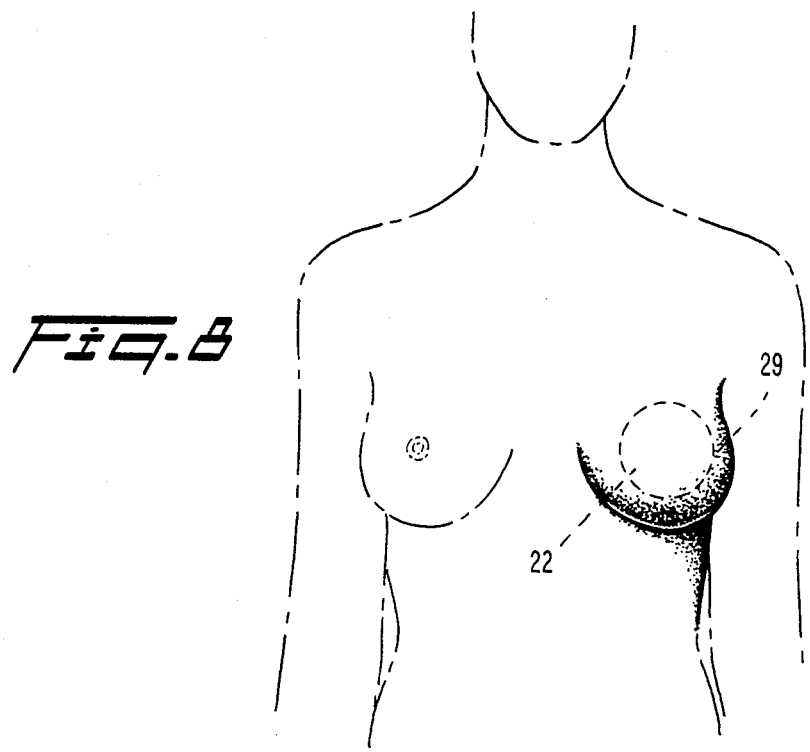
FIG. 8 is an anatomical view showing a breast after mastectomy and a collapsed implant according to the present invention in position.
Figure 9:
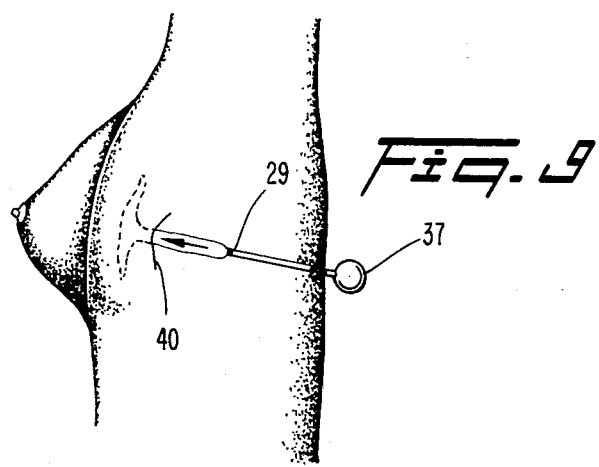
FIG. 9 is a side view of FIG. 8 and showing a filling tube and reservoir being placed beneath the skin adjacent the implant.
Figure 10:
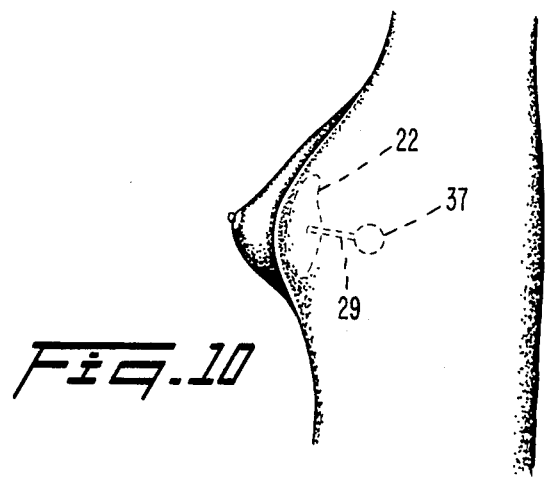
FIG. 10 is a view similar to FIG. 9 showing the filling tube and reservoir in place beneath the skin.

The device of the present invention is useful in performing primary breast reconstruction following subcutaneous mastectomy. A pocket is formed in the subpectoral plane by making a lateral incision 46 and a deflated implant 22 is placed in the pocket. The implant 22 is shown in broken lines in FIGS. 8 and 9 and the filling tube 29 and reservoir 37 are shown in FIG. 9 prior to complete insertion and implantation beneath the skin. After implantation is complete (FIG. 10), approximately 100-200 cc of saline is added by percutaneous injection using a syringe 41 and needle 43 (FIG. 11). Excessive pressure on thin skin flaps is avoided by adding only a small amount of saline at this point. If excessive pressure appears on the flaps, saline can be removed prior to the patient leaving the operating room.

Complete expansion of the implant may require a period of about four to eight weeks. It may be desirable to overexpand the implant 22 and the skin flaps by about 10% and then remove some of the saline percutaneously to achieve the desired prosthesis size as this results in a very smooth and natural contour to the reconstructed breast.

Following complete mastectomy for carcinoma in situ or early carcinoma, immediate breast reconstruction can be carried out by placing a deflated implant beneath the pectoralis major muscle. A small amount, i.e., 100-200 cc, of saline is added, and it is necessary to insure that there is no pressure on the compromised skin flaps before beginning further expansion. Once viability of the skin flaps is assured, usually 2-3 days following surgery, inflation of the implant by percutaneous injection can begin. The present invention readily accommodates this procedure as the implant, filling tube and reservoir can be implanted immediately following surgery and inflation of the implant can begin anytime thereafter with a minimum of inconvenience, pain, and danger of infection to the patient.

Following radical mastectomy and flap reconstruction, a deflated implant 22 is placed beneath the pectoralis major muscle and expansion carried out by subcutaneous injections into a reservoir 37. In this manner, not only is the tissue and the muscle of the chest wall expanded, but also the flap is expanded. Expansion and thinning of the skin flap results in a smoother flap-recipient junction and a more natural looking breast.

In the embodiment of FIG. 13, an inflatable implant 122 is provided with an inlet opening 123 and a retention valve 124. The valve 124 includes a double flap member 125 which extends inwardly of the implant 122 from the inlet opening 123 which is formed as a slit 126 in a cover flap 120.

A filling tube 129 has one end 131 detachably connected to the implant by insertion through the slit 126 in the valve flap 120 and passage through the double flap valve member 119 beyond the end thereof as shown in FIG. 13. In this position of the parts, the implant 122 can be inflated and expanded. A reservoir (not shown) is fixed to the other end of the filling tube 129. As was the case in the embodiment of FIGS. 1-12, expansion of the implant 122 after implantation can be performed by percutaneous injection into the reservoir. Removal of saline from the implant 122 is also carried out in the same manner as above.

Upon achieving the desired expansion, the reservoir and filling tube 129 are removed by making a single incision in the skin over the reservoir and pulling on the reservoir and filling tube causing the latter to detach from the implant 122. Upon removal of the filling tube 129, the valve 124 closes and the implant 122 remains in place permanently.

By the foregoing, there has been disclosed a delayed filling permanent reconstruction implant and a method of performing human tissue expansion and providing a permanent reconstruction implant calculated to fulfill the inventive objects herein. While preferred embodiments of this invention are illustrated and described in detail herein, it will be understood that various additions, substitutions, modifications and omissions can be made to the present invention without departing from the scope of spirit of the invention. Thus, it is intended that the present invention cover the additions, substitutions, modifications and omissions provided they come within the scope of the appended claims and their equivalents.

What is claimed is:

1. A delayed filling permanent reconstruction implant comprising an inflatable flexible plastic prosthesis constructed substantially entirely of a relatively soft and flexible material adapted to be implanted beneath human tissue, said prosthesis having an inlet opening, a normally closed valve in said opening, a filling tube having one end detachably connected to said prosthesis at said inlet opening and operable when in said opening to open said valve, and a reservoir connected to the other end of said filling tube, whereby said prosthesis can be controllably expanded after implantation by percutaneously injecting fluid into said reservoir which fluid passes through said filling tube into said prosthesis, said filling tube and reservoir both readily detachable from the prosthesis upon achieving the desired expansion thereof and said opening forming a relatively smooth exterior surface upon detachment of said filling tube therefrom whereupon said valve closes and said prosthesis remains permanently implanted.

2. The device claimed in claim 1, said filling tube and said reservoir being adapted to be placed beneath the skin near said prosthesis, said prosthesis being expandable by percutaneous injection of fluid into said reservoir, said reservoir and filling tube being detachable from said prosthesis and removable through a single incision over said reservoir.

3. The device claimed in claim 1, said reservoir being constructed substantially entirely of a relatively soft and flexible material facilitating easy removal from beneath the skin.

4. The device claimed in claim 1, said inlet opening and valve being located at a lateral position of said prosthesis.

5. A delayed filling permanent reconstruction implant comprising an inflatable flexible plastic prosthesis adapted to be implanted beneath human tissue, said prosthesis having an inlet opening, a normally closed valve in said opening, a filling tube having one end detachably connected to said prosthesis at said inlet opening and operable when in said opening to open said valve, and a reservoir connected to the other end of said filling tube, whereby said prosthesis can be controllably expanded after implantation by percutaneously injecting fluid into said reservoir which fluid passes through said filling tube into said prosthesis, said filling tube and reservoir both readily detachable from the prosthesis upon achieving the desired expansion thereof, whereupon said valve closes and said prosthesis remains permanently implanted, said valve including a valve tube extending inwardly of said inlet opening, a diaphragm normally covering said valve tube, said diaphragm having openings therein which are blocked when said diaphragm covers said valve tube, said diaphragm being movable away from said valve tube upon insertion of said one end of said filling tube into said inlet opening and through said valve.

6. The device claimed in claim 5, said filling tube having a shoulder adjacent said one end limiting insertion thereof.

7. A delayed filling permanent reconstruction implant comprising an inflatable flexible plastic prosthesis adapted to be implanted beneath human tissue, said prosthesis having an inlet opening, a normally closed valve in said opening, a filling tube having one end detachably connected to said prosthesis at said inlet opening and operable when in said opening to open said valve, and a reservoir connected to the other end of said filling tube, whereby said prosthesis can be controllably expanded after implantation by percutaneously injecting fluid into said reservoir which fluid passes through said filling tube into said prosthesis, said filling tube and reservoir both readily detachable from the prosthesis upon achieving the desired expansion thereof, whereupon said valve closes and said prosthesis remains permanently implanted, said valve including a normally closed, double flap construction extending inwardly of said prosthesis at said inlet opening, a cover flap over said inlet opening having a slit therein, said one end of said filling tube being insertable through said slit and said double flap.

8. A method of performing human tissue expansion and providing a permanent reconstruction implant comprising the steps of providing a permanent prosthesis having an inlet opening, a normally closed valve in said opening, providing a filling tube having one end adapted for insertion into said inlet opening to open said valve and having a self-sealing reservoir at its other end, surgically placing the prosthesis in the area to be reconstructed and placing the filling tube and reservoir beneath the skin adjacent the prosthesis with the tube one end in the inlet opening, gradually expanding the prosthesis by percutaneous fluid injections into the reservoir, and detaching the reservoir and filling tube from the prosthesis and allowing the prosthesis to remain permanently in position.

* * * * *